United States Patent [19]

Calabresi et al.

[11] Patent Number: 4,950,466

[45] Date of Patent: Aug. 21, 1990

[54] REDUCTION OF THE SEVERITY OF 3'-AZIDO-3'-DEOXYTHYMIDINE-INDUCED ANEMIA USING A COMBINATION OF BENZYLACYCLOURIDINE AND DIPYRIDAMOLE

[76] Inventors: Paul Calabresi, 27 Glen Ave.; James W. Darnowski, 6 Calderone St., both of Barrington, R.I. 02806; Michael C. Wiemann, 11 Villa Ave., Providence, R.I. 02906

[21] Appl. No.: 210,882

[22] Filed: Jun. 22, 1988

[51] Int. Cl.$^5$ .................... A61K 47/00; A61K 31/505
[52] U.S. Cl. ...................................... 424/10; 514/258; 514/922
[58] Field of Search ................... 424/10; 514/922, 258

[56] References Cited

PUBLICATIONS

Chemical Abstracts 108(9):68364, El Kouni et al., 1987.
El Kouni et al., "Metabolism of Adenosine Analogues by Schistosoma Mansoni and the Effect of Nucleoside Transport Inhibitors", *Biochemical Pharmacology*, 36, 7, pp. 1099–1106, 1987.

*Primary Examiner*—Douglas W. Robinson
*Assistant Examiner*—Raymond J. Henley, III.
*Attorney, Agent, or Firm*—Thompson, Hine and Flory

[57] ABSTRACT

The invention is directed to a method of inhibiting anemia caused by the administration of AZT to a patient which comprises administering to said patient an effective anemia-inhibiting amount of a combination of dipyridamole and 5-benzylacyclouridine. The invention is further directed to a pharmaceutical composition comprising as the active pharmaceutical agent a combination of dipyridamole and 5-benzylacyclouridine in association with a pharmaceutically acceptable carrier or diluent.

6 Claims, No Drawings

REDUCTION OF THE SEVERITY OF 3'-AZIDO-3'-DEOXYTHYMIDINE-INDUCED ANEMIA USING A COMBINATION OF BENZYLACYCLOURIDINE AND DIPYRIDAMOLE

BACKGROUND OF THE INVENTION

3'-Azido-3'-deoxythymidine (AZT) is the only drug which is commercially available for the treatment of the acquired immune deficiency syndrome (AIDS) or symptomatic advanced AIDS-related complex (ARC). AZT inhibits the human immunodifficiency virus reverse transcriptase.

The main toxic affect of AZT in patients receiving the drug is severe anemia, often associated with a megaloblastic bone marrow (Yarchoan, et al., Lancet, 1986, 1:575).

AZT was found to consistently inhibit granulocyte macrophage colony forming cells and erythroid burst-forming cells in dose-dependent fashion in vitro (Sommadossi and Carlisle, Antimicrobial Agents Chemo., 1987, 31:453–454). The authors concluded that since prolonged AZT therapy will probably be required by an AIDS patient, such patients will be subject to increased myelosuppression.

In studies carried out in vitro to "rescue" human bone marrow progenitor (HBMP) cells using potential rescue agents, Sommadossi, et al., found that uridine and cytidine could reverse the toxic effect of AZT in HBMP cells. (Sommadossi, Carlisle, Schinazi, et al., Twenty-Seventh Intersci. Conf. Antimicrob. Agents Chemother. 1987; 27:163.)

While uridine is able to reverse the toxic effect of AZT on HBMP cells in vitro, unfortunately, uridine is deleterious to humans when given in vivo. When uridine is administered to a patient in an intermittant schedule, it is rapidly eliminated from the plasma. Continuous infusion of uridine is associated with rapid and potentially dangerous rises in body temperature. (See van Groeninger, et al., Cancer Treatment Rept., 70:745–750, 1986.)

The acyclouridine 5-benzylacylouridine (BAU) is an inhibitor of the enzyme uridine phosphorylase which is responsible for the cleavage of uridine to uracil. (Niedzwicki, et al., Biochem. Pharmacol., 1982, 31:1857–1861.) BAU also inhibits the cleavage of the antineoplastic 5-fluoro-2'-deoxyuridine (Fd Urd) used in cancer chemotherapy because of its inhibition of the action of uridine phosphorylase (Chu, et al., Cancer Res., 1984, 44:1852–56.)

Dipyridamole (DPR) 2,6-(diethanol-amino)-4,8-dipyridino-pyridino-(5,4-d)pyrimidine is a platelet inhibitor which is used in prophylaxis of thromboembolism after cardiac valve replacement. (PDR®, 42nd Ed., 1988, p.725.) There is also evidence which indicates that dipyridamole may inhibit the efflux of uridine from the cell. (Grem and Fisher, Cancer Res., 1986, 46:6191–6199; Grem and Fisher, Cancer Res., 1985, 45:2967–2972.)

It has been found that administration of a combination of BAU and dypyridamole to animals receiving AZT reduces the severity of AZT-induced anemia. Animals which were treated with AZT and with a combination of BAU and dipyridamole did not develop severe suppression of hemoglobin or hematocrit as did animals treated only with AZT. Administration of a combination of BAU/DPR is expected to produce a rise in the reticulocyte count, hemoglobin and hematocrit of patients which have previously been made anemic by administration of AZT.

SUMMARY OF THE INVENTION

The invention is directed to a method of reducing anemia produced by the administration of AZT to a patient receiving AZT which comprises administering to said patient an effective anemia inhibiting amount a combination of 5-benzylacyclouridine and dipyridamole.

DETAILED DESCRIPTION OF THE INVENTION

The invention is directed to a method of inhibiting anemia caused by the administration of AZT to a patient which comprises administering to said patient an effective anemia-inhibiting amount of a combination of 5-benzylacyclouridine and dipyridamole. The invention is further directed to a pharmaceutical composition comprising as the active pharmaceutical agents the compounds 5-benzyl-acyclouridine and dipyridamole in combination with a pharmaceutically acceptable carrier or diluent.

The preparation of 5-benzylacyclouridine is known in the art and is described in Niedzwicki, et al., Biochem. Pharmacol., 1982, 31:1857–1861. BAU may be administered by conventional administration routes, for example, orally, intravenously, intraperitoneally and subcutaneously. The preferred route of administration of BAU in the method of the invention is by oral administration.

The precise dosage level of BAU will depend upon factors recognized by the skilled clinician, for example, general patient health, body weight, sex, and the like. Generally, BAU should be administered from about 10 to about 75 mg/kg/day. Preferably from about 10 to about 30 mg/kg/day and more preferably at about 20 mg/kg/day.

Although the use of 5-benzylacyclouridine in the method of the invention is specifically described herein, any pharmaceutically acceptable compound which inhibits the enzyme uridine phosphorylase is expected to be useful in the practice of the method of the invention. Such compounds, as for example, 5-benzyl-1-[1,3-dihydroxy-2-propoxy)methyl] uracil and 5-(m-benzyloxy-benzyl)-1-[1,3-dihydroxy-2-propoxy)methyl] uracil disclosed in U.S. Pat. No. 4,613,604 are contemplated for use in the invention method.

Dipyridamole is commercially available under the trade name "PERSANTINE", from Boehringer Ingelheim Pharmaceuticals, Inc., Ridgefield, Conn. 06877. The preparation of the compound is described in British Pat. No. 807,826. Chemically, dipyridamole is 2,2',2"2"'-(4,8-dipiperidinopyimidol[5,4-d]pyrimidene-2,6-diyldinitrilo) tetraethanol.

Dipyridamole is a platelet adhesion inhibitor, although the mechanism of action has not been fully elucidated. The mechanism may relate to inhibition of red blood cell uptake of adenosine, itself an inhibitor of platelet reactivity, phosphodiesterase inhibition leading to increased cyclic-3',5'-adenosine monophosphate within platelets, and inhibition of thromboxane $A_2$ formation which is a potent stimulator of platelet activation. Dipyridamole is indicated as an adjunct to coumarin anticoagulants in the prevention of postoperative thromboembolic complications of cardiac valve replacement.

Dipyridamole may be administered orally or intravenously. The usual adult prescribing limit is up to 400 mg per day. From about 60 mg to about 200 mg may be given 3-6 times per day. The recommended dosage is 75-100 mg four times daily.

3'-Azido-3'-deoxythymidine (AZT) is commercially available under the tradename "RETROVIR" from the Burroughs Wellcome Company, Research Triangle Park, N.C. AZT should be administered to a patient in need of treatment according to the dosage and administration schedule set out in the Package Insert for said product. The recommended starting dose of AZT is 200 mg administered orally every 4 hours around the clock.

The following detailed examples provide further illustration of the practice of the method of the invention.

EXAMPLE 1

For oral administration, BAU was dissolved in water to achieve a final concentration of 0.3 mg/mL. For intraperitoneal administration, BAU was dissolved in dimethylsulfoxide (DMSO) to achieve final concentrations of 60, 100, or 120 mg/mL.

AZT produced by Burroughs Wellcome Co., 100 mg capsule, was dissolved in water 50° C. The solution was centrifuged at 15,000 rpm for 20 minutes. The supernatant was then diluted with water to achieve a final concentration of 1 mg/mL of AZT. The concentration was verified by spectrophotomer (maximum absorbance: 267).

Female Balb/c mice, 6-12 weeks old, were purchased from the Animal Care Facility of the Roger Williams Cancer Center. The animals were randomly divided into eight groups. Six of the treatment protocols were performed in duplicate. Each group contained either eight or nine animals. The animals were weighed once weekly. Food and water was available ad libitum. Blood samples were obtained from the tail vein. The first blood sample was obtained on Day 0 and subsequent samples were obtained on Days 19, 27, 34 and 44, 48, 54 and 68 after the initiation of drug treatment. With each sampling, approximately 100 ul of blood was removed from each animal. The blood obtained from the animals in each group was pooled and analyzed by Coulter Counter. On each sample, hemoglobin, hematocrit, and white blood cell count were determined. The mean red cell volume was calculated. The Treatment Groups were as follows:

Group 1—Control

Group 2—AZT administered in the drinking water (1 mg/mL). This corresponds to an administered dose of 145 mg/kg/day. DMSO was given ip, 0.01 mL/5 grams body weight, once weekly.

Group 3—AZT administered in the drinking water (1 mg/mL).

Group 4—BAU 240 mg/kg, ip, once weekly.

Group 5—AZT administered in the drinking water (1 mg/mL) and BAU 240 mg/kg, ip, once weekly.

Group 6—AZT administered in the drinking water (1 mg/mL) and BAU 120 mg/kg, ip, twice weekly.

Group 7—AZT administered in the drinking water (1 mg/mL) and BAU administered in the same container of drinking water (0.3 mg/mL). This corresponds to a daily administered dose of 43 mg/kg. The bioavailability of BAU administered orally was 80%. Therefore, the bioavailable dose of BAU administered to this group was 240 mg/kg/week.

Group 8—Dipyridamole (DPR) was administered by the oral route in drinking water. The concentration was 0.69 mg/ml which corresponds to an administered dose of 100 mg/kg/day.

Group 9—DPR was administered by the oral route in drinking water (0.69 mg/mL), which corresponds to an administered dose of 100 mg/kg/day; AZT (1 mg/mL) was administered in the drinking water.

Group 10—DPR was administered by the oral route in drinking water (0.69 mg/mL), which corresponds to an administered dose of 100 mg/kg/day; AZT (1 mg/ml) administered in drinking water; BAU was administered intraperitoneally (i.p.) 120 mg/kg/twice weekly.

The results are summarized in Table 1.

TABLE 1

| TREATMENT GROUP | DAY 0 | | | DAY 19 | | | DAY 27 | | | DAY 34 | | | DAY 44 | | |
|---|---|---|---|---|---|---|---|---|---|---|---|---|---|---|---|
| | Hb | Hct | WBC | Hb | Hct | WBC | Hb | Hct | WBC | Hb | Hct | WBC | Hb | Hct | WBC |
| 1 | 17.6 | 50.0 | 8.8 | 17.2 | 50.5 | 9.03 | 16.5 | 52 | 8.7 | 17.8 | 59 | 13.6 | — | — | — |
| 2 | 17.3 | 49.0 | 10.1 | 12.8 | 36.0 | 21.2 | 13 | 40 | 11.6 | 11.6 | 35 | 11.5 | — | — | — |
| 3 | 17.3 | 43.0 | 8.4 | 13.7 | 43.0 | 17.7 | 13.6 | 43 | 13.6 | 13.9 | 42 | 13.3 | — | — | — |
| 4 | 18.3 | 52.0 | 8.8 | 17.3 | 50.0 | 10.8 | 16.2 | 51 | 6.6 | 17.2 | 50 | 7.9 | — | — | — |
| 5 | 17.1 | 50.0 | 9.2 | 14.3 | 42.0 | 23.1 | 14.1 | 44 | 7.9 | 14.2 | 43 | 11.4 | — | — | — |
| 6 | 18.0 | 51.0 | 10.1 | 14.8 | 43.0 | 19.6 | 13.8 | 44 | 10.2 | 14.6 | 45 | 23.1 | — | — | — |
| 7 | 17.6 | 50.0 | 7.6 | 14.8 | 42.0 | 15.7 | 14.4 | 43 | 8.2 | 15.3 | 45 | 23.4 | — | — | — |
| 8 | 16.5 | 48.0 | 5.9 | 14.3 | 49 | 11.1 | 15.5 | 45 | 10 | 14.8 | 45 | 9.4 | 14.6 | 45 | 9.1 |
| 9 | 16.4 | 48.5 | 7.0 | 14.3 | 43.1 | 6.3 | 14.6 | 43.5 | 9.1 | 13.8 | 40 | 8.4 | 14.7 | 44.5 | 8.1 |
| 10 | 16.1 | 48.0 | 6.8 | 15 | 44.2 | 8.7 | 14.2 | 43.5 | 8.9 | 13.8 | 44 | 13.8 | 14.3 | 44 | 9.7 |

| TREATMENT GROUP | DAY 48 | | | DAY 54 | | | DAY 68 | | |
|---|---|---|---|---|---|---|---|---|---|
| | Hb | Hct | WBC | Hb | Hct | WBC | Hb | Hct | WBC |
| 1 | 16.4 | 49.0 | 11.7 | — | — | — | — | — | — |
| 2 | 11.0 | 33 | 5.0 | — | — | — | — | — | — |
| 3 | 13.2 | 34 | 5.6 | — | — | — | — | — | — |
| 4 | 16.6 | 49 | 6.4 | — | — | — | — | — | — |
| 5 | 12.5 | 39 | 5.7 | — | — | — | — | — | — |
| 6 | 13.1 | 40 | 6.6 | — | — | — | — | — | — |
| 7 | 13.0 | 42 | 8.3 | — | — | — | — | — | — |
| 8 | — | — | — | 15.4 | 46 | 7.6 | 15.7 | 45 | 9.3 |
| 9 | — | — | — | 15.2 | 45.5 | 9.8 | 14.6 | 42.5 | 6.9 |
| 10 | — | — | — | 15.1 | 46.5 | 8.7 | 14.1 | 41.5 | 7.5 |

The anemia produced by AZT in mice is typical of AZT induced anemia in humans. The anemia induced by AZT is often megaloblastic. Megaloblastic anemias are characterized by red blood cells with an increased mean corpuscular volume (MCV).

Body weights of the animals in the treatment groups were measured each week. Generally, animals receiving only AZT tended to lose weight as their anemia increased over time. Animals receiving AZT, BAU and dipyridamole tended to maintain thier body weights over time.

Administration of BAU and dipyridamole to an already anemic animal is expected to result in the stimulation of the production of reticulocytes (young red blood cells) which should result in a subsequent rise in the hemoglobin of the animal. Thus, the administration of BAU and DPR to an animal receiving AZT will reduce or eliminate AZT induced anemia. Further, the anemia which is caused by the administration of AZT to an animal can be reversed once the anemic condition is present.

The pharmaceutical compositions of the invention comprise a combination of dipyridamole and BAU in association with a pharmaceutically acceptable excipient, which can be a carrier or a diluent. The pharmaceutical compositions of the invention are prepared following conventional methods and are administered in a pharmaceutically suitable form.

The pharmaceutical compositions of the invention can be administered in a variety of dosage forms, e.g., orally, in the form of tablets, capsules, sugar, or film-coated tablets, liquid solutions or suspensions, rectally, in the form of suppositories, parenterally, e.g., intramuscularly or by intravenous injection or infusion. The preferred pharmaceutical composition of the invention is one which may be orally administered. Another preferred pharmaceutical composition of the invention is a intravenous composition.

The exact dosage regimen of BAU and dipyridamole which is useful in the compositions of the invention will depend on factors which would be recognized by the skilled artisan, e.g., the progression of the AIDS disease, age, weight, other conditions of the patient and administration route.

The solid oral forms of the composition of the invention may contain, together with the active agents, diluents, e.g., lactose, dextrose, saccharose, cellulose, corn starch or potato starch; lubricants, e.g., silica, talc, stearic acid, magnesium or calcium stearate, and/or polyethylene glycols; binding agents, e.g., starches, arabic gums, gelatin, methylcellulose, carboxymethylcellulose or polyvinyl pyrrolidone; disaggregating agents, e.g, a starch, alginic acid, alginates or sodium starch glycolate, effervescing mixtures; dyestuffs; sweeteners; wetting agents, such a lecithin, polysorbates, laurylsulphates; and; in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

The liquid dispersions for oral administration may be, e.g., syrups, emulsions, and suspensions. The syrups may contain as carrier, for example, saccharose or saccharose with glycerine and/or mannitol and/or sorbitol; in particular a syrup to be administered to diabetic patients can contain as carriers only products not metabolizable to glucose, or metabolizable in very small amount to glucose, for example, sorbitol.

The suspensions and the emulsions may contain as carrier, for example, a natural gum, agar, sodium alginate, pectin, methylcellulose, carboxymethylcellulose, or polyvinyl alcohol. The suspensions or solutions for intramuscular injections may contain together with the active compound a pharmaceutically acceptable carrier, e.g., sterile water, olive oil, ethyl oleate, lycols, e.g., propylene glycol, and if desired, a suitable amount of lidocaine hydrochloride.

The solutions for intravenous injections or infusions may contain a carrier, for example, sterile water or preferably they may be in the form of sterile, aqueous, isotonic saline solutions.

The suppositories may contain together with the active compound a pharmaceutically acceptable carrier, e.g, cocoa butter, polyethylene glycol, a polyoxyethylene sorbitan fatty acid ester surfactant or lecithin.

Having described the invention in detail and by reference to the preferred embodiments thereof, it will be apparent that modifications and variations are possible without departing from the spirit and scope of the invention defined in the appended claims.

What is claimed:

1. A pharmaceutical composition comprising as the active pharmaceutical agent a combination of dipyridamole and 5-benzylacyclouridine in association with a pharmaceutically acceptable carrier or diluent said dipyridamole and said 5-benzylacyclouridine being present in amounts sufficient to reduce anemia associated with the administration of a 3'-azido-3'deoxythymidine.

2. A method of inhibiting anemia in a patient having 3'-Azido-340 -deoxythymidine-induced anemia, which comprises administering to said patient an effective anemia-inhibiting amount of a combination of 5-benzylacyclouridine and dipyridamole.

3. A method according to claim 2, wherein said patient is a human patient.

4. A method according to claim 2, wherein 3'-Azido-3'deoxythymidine is administered orally, wherein dipyridamole is administered orally and 5-benzylacyclouridine is administered orally, intramuscularly or intravenously.

5. A method according to claim 4, wherein dipyridamole is administered orally and 5-benzylacyclouridine is administered intravenously.

6. A method according to claim 3 wherein from about 200 mg to about 300 mg of 3'-Azido-3'-deoxythymidine is administered to said patient every 4 to 6 hours; wherein from about 60 mg to about 200 mg of dipyridamole is given to said patient 3-6 times per day; and wherein about 10 mg/kg/day to about 75/mg/kg/day of 5-benzylacyclourdine is administered to said patient.

* * * * *

UNITED STATES PATENT AND TRADEMARK OFFICE
CERTIFICATE OF CORRECTION

PATENT NO. : 4,950,466
DATED : August 21, 1990
INVENTOR(S) : Paul Calabresi et al.

It is certified that error appears in the above-identified patent and that said Letters Patent is hereby corrected as shown below:

Column 6, line 40, delete "3'-Azido-340-" and insert --3'-Azido-3'- --.

Column 6, line 60, delete "5-benzylacyclourdine" and insert --5-benzylacyclouridine--.

Signed and Sealed this

Nineteenth Day of January, 1993

Attest:

DOUGLAS B. COMER

Attesting Officer

Acting Commissioner of Patents and Trademarks